United States Patent
Talwai et al.

(10) Patent No.: US 10,292,585 B1
(45) Date of Patent: May 21, 2019

(54) MENTAL STATE MEASUREMENT USING SENSORS ATTACHED TO NON-WEARABLE OBJECTS

(71) Applicant: X Development LLC, Mountain View, CA (US)

(72) Inventors: Preeti Murali Talwai, El Dorado Hills, CA (US); Michael Patrick Bauerly, Sunnyvale, CA (US); Johan Ulrich Lewin Jessen, Mountain View, CA (US); Matthew David Day, Oakland, CA (US)

(73) Assignee: X Development LLC, Mountain View, CA (US)

( * ) Notice: Subject to any disclaimer, the term of this patent is extended or adjusted under 35 U.S.C. 154(b) by 201 days.

(21) Appl. No.: 15/390,193

(22) Filed: Dec. 23, 2016

(51) Int. Cl.
*A61B 5/00* (2006.01)
*A61B 5/04* (2006.01)

(52) U.S. Cl.
CPC . *A61B 5/00* (2013.01); *A61B 5/04* (2013.01)

(58) Field of Classification Search
CPC .................................... A61B 5/00; A61B 5/04
See application file for complete search history.

(56) References Cited

U.S. PATENT DOCUMENTS

| | | |
|---|---|---|
| 8,903,176 B2 | 12/2014 | Hill |
| 9,182,891 B2 | 11/2015 | Adarrage |
| 2008/0221401 A1 | 9/2008 | Dercak et al. |
| 2009/0270692 A1* | 10/2009 | Hyde ........................ A61B 5/00 600/301 |
| 2013/0102854 A1* | 4/2013 | Zheng ..................... A61B 5/00 600/300 |
| 2014/0051044 A1* | 2/2014 | Badower .................. A61B 5/00 434/236 |
| 2014/0107531 A1 | 4/2014 | Baldwin |
| 2014/0201207 A1 | 7/2014 | Sadowsky |
| 2014/0323817 A1 | 10/2014 | Kaliouby et al. |

(Continued)

OTHER PUBLICATIONS

'health.usnews.com' [online]. "Wearable Technology Gets Emotional," Jul. 2015, [retrieved on Dec. 22, 2016] Retrieved from Internet: URL<http://health.usnews.com/health-news/health-wellness/articles/2015/07/09/wearable-technology-can-now-detect-your-emotions>.

(Continued)

*Primary Examiner* — Jason Skaarup
(74) *Attorney, Agent, or Firm* — Fish & Richardson P.C.

(57) ABSTRACT

This specification describes technologies for mental state measurement using sensor data obtained from sensors attached to objects. One embodiment is a method that includes receiving sensor data from sensors attached to non-wearable objects. The first and second attachable sensors each include an output and a sensor. The method further includes determining mental state data from the sensor data; and causing to be displayed a representation of a mental state based on the mental state data. The method can further include: deriving an action metric from the mental state data; comparing the action metric to a threshold; automatically taking an action when the action metric exceeds the threshold; collecting post action sensor data; determining post action mental state data based at least in part on the post action sensor data; and forwarding the post action mental state data for display of a representation of a mental state.

17 Claims, 9 Drawing Sheets

(56) References Cited

U.S. PATENT DOCUMENTS

| | | |
|---|---|---|
| 2015/0142553 A1 | 5/2015 | Kodra et al. |
| 2016/0132755 A1 | 5/2016 | Ikeda |
| 2017/0109571 A1* | 4/2017 | McDuff ............. G06K 9/00302 |
| 2017/0113057 A1* | 4/2017 | Goodall ................. A61N 2/006 |

OTHER PUBLICATIONS

Quazi. "Human emotion recognition using smart sensors," Massey University, New Zealand, 2012, 122 pages.

* cited by examiner

MENTAL STATE MEASUREMENT USING SENSORS ATTACHED TO NON-WEARABLE OBJECTS

BACKGROUND

Technical Field

This specification relates to mental state measurement using sensor data obtained from sensors attached to objects.

Background

If a relevant individual, e.g., an employee, event organizer or presenter, knows the mental state of a group, e.g., a work group, event attendees or audience, the individual and the group can function better. An individual can spend time trying to determine the mental state of a group for example through observation and by asking questions of members of the group. However, doing so is time consuming and the accuracy of the results will vary dramatically depending on the individual, the group and the context. Thus there is a need for more accurate, scalable and less intrusive methods for measuring the mental state of a group.

In addition, individuals spend an increasing amount of time interacting with smart devices, i.e., devices that have computing power, many of which are connected to the internet. There is a need for improved methods for incorporating the mental state of individuals or groups into human-computer interaction.

SUMMARY

This specification describes technologies for mental state measurement using sensor data obtained from sensors attached to objects. In general, one innovative aspect of the subject matter described in this specification can be embodied in a method that includes receiving, at a mental state measure system having a mental state data processor, sensor data from a first attachable sensor attached to a first non-wearable object and a second attachable sensor attached to a second non-wearable object. The first and second attachable sensors are each configured to attach to a non-wearable object after the object has been manufactured. The first and second attachable sensors each include an output and a sensor. The method further includes determining, by the mental state data processor, mental state data from the sensor data; and forwarding, by the mental state measurement system, the mental state data for display of a representation of a mental state.

The method can further include: deriving an action metric from the mental state data; comparing the action metric to a threshold; automatically taking an action when the action metric exceeds the threshold; collecting post action sensor data; determining post action mental state data based at least in part on the post action sensor data; and forwarding the post action mental state data for display of a representation of a mental state. Automatically taking an action can include providing a recommendation, by the mental state measurement system, to at least one member of the group to relocate based on the mental state data. The method can further include using at least one of the post action sensor data and the post action mental state data in determining which action to take automatically in the future.

The first attachable sensor can be configured to detect sensor data associated with at least a first member of a group and the second attachable sensor can be configured to detect sensor data associated with at least a second member of the group. In certain embodiments, the first attachable sensor provides an output to the user in response to at least one of mental state data and sensor data.

The method can further include altering properties of a communication device associated with a member of the group in response to at least one of mental state data and sensor data associated with the member. The group can be a group of people associated with a location and the method can further include displaying the mental state data for a location based on the mental state of the group associated with that location.

In certain embodiments, the method can include receiving sensor data from a sensor that is connected to a bone conduction device. The non-wearable objects can be objects that do not have sensors prior to attaching the attachable sensors. In such a situation, the first attachable sensor can be attached using an adhesive strip.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The subject matter described in this specification can be implemented in particular embodiments so as to realize one or more of the following advantages. Embodiments enable measurement of the mental state of individuals and groups. Integrating attachable sensors and adaptable objects (e.g., objects that adapt to a signal indicative of a user mental state) into a mental state measurement system encourages the use of devices with sensors. Increased use of devices with sensors in turn results in greater accuracy in measuring mental state data of individuals and groups.

Individual and group mental state data can be used to improve human-device interaction. For example, if a mental state measurement system detects that an individual is focused, and thus productive, the individual's display can be modified to reduce distractions. Conversely, if a mental state measurement system detects that an individual or group is bored, the system can provide a recommended action via a display such as a display designed for viewing by groups or a display on an adaptable object. In certain embodiments, the mental state measurement system can react to: noise levels, by dimming the lights or changing the hues, team fatigue, by automatically raising all electric desks, errors and concentration issues, by introducing forced breaks (auto-locking displays and notifying users to take a break for 10 mins) individuals stress levels, by choosing activities that lowers stress (e.g. suggesting that a user listen to 10 minutes of calming music). One of many useful aspects to this measure-prompt change-remeasure system is how the mental state measurement system gets more effective over time. The mental state measurement system will keep track of what works for whom and when, and adapt to situations over time to prompt the most effective changes.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

If an individual, e.g., an employee, event organizer or presenter, knows his own mental state or the mental state of a group, e.g., a work group, event attendees or audience, the individual and the group can function better. Similarly, if computing systems with which the individual or group interacts can detect the mental state of the individual or group, those systems can adapt so as to improve the interaction between the individual and the system.

Individuals spend an increasing amount of time interacting with smart devices, i.e., devices that have computing power, many of which are connected to the internet and many of which have sensors. Moreover, the adoption of sensors is constantly increasing for a variety of reasons. Thus, in the instance where a user consents, or a group of users consent, to the use of sensor data for measuring mental state and to use of the sensor data to improve a variety of interactions as a result, the data may be used for measuring the mental state of an individual, and of a group to which the individual belongs.

The mental state measurement (MSM) system can use data processing techniques so that individual data cannot be derived from group results. In addition, objects with sensors (especially non-obvious ones such as a mug) may have standardized visuals indicating that a sensor is operating (similar to a red recording light on a camera). Furthermore, such sensors may be deactivated during non-work hours. In addition, an object with a sensor can show that it is live and allow a user to stop interacting with it. For example, in one embodiment a user can pick up a sensing coffee mug, and the rim around the coffee mug is configured to light up sequentially in the shape of a circle where the full circle is not completed for 3 secs. If the user puts the cup down before the rim is completely lit up, the sensing is cancelled.

According to one embodiment, a variety of sensors, including sensors attached to adaptable objects, gather sensor data for a group of people, e.g., a set of team members or people in a particular location, and transmit the sensor data to a MSM system. The MSM system receives the sensor data and determines mental state data for the group or location based on the sensor data. The MSM system then takes an action based on the mental state data and forwards the mental state data for display of a representation of a mental state.

Figure 1:
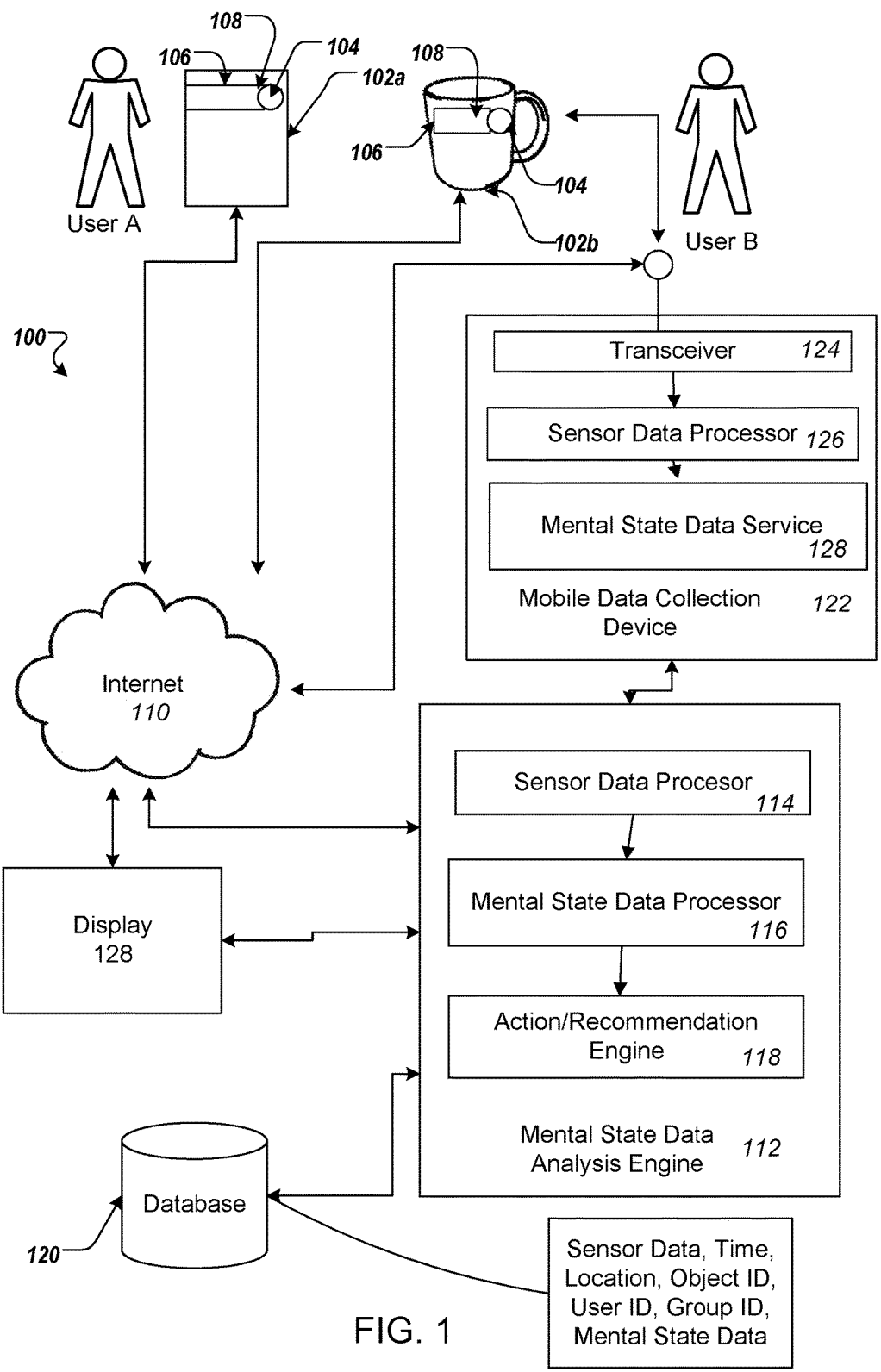
FIG. 1 is a schematic of an exemplary mental state measurement system communicating with attachable sensors attached to non-wearable objects.

FIG. 1 is a schematic of an exemplary MSM system 100 communicating with a variety of attachable sensors 108 attached to non-wearable objects 102. The attachable sensors 108 include at least one sensor 104 and one output 106.

In one embodiment, the MSM system interacts with a plurality of sensors. The sensors can be attachable sensors attached to objects, e.g., attached to non-wearable objects, after the objects are manufactured, after the objects are distributed, or after the objects are sold. The sensors can also be integrated into devices at the time of manufacture.

In the embodiment illustrated in FIG. 1, attachable sensors 108 are attached to an electronic notebook 102*a* and a coffee mug 102*b*, respectively. The attachable sensors attach to an object using, for example, an adhesive-strip. A user, e.g., user A, can identify the object, e.g., a notebook 102*a*, to the mobile data collection device 122 or the mental state data analysis engine 112, for example at the time that the user attaches the sensor to the object.

In order for the MSM system to identify objects that have sensors attached, objects can have a built-in interface (e.g. a micro-usb) to allow the sensor to pair to the object or there can be a manual setup process (e.g., a customer can take a photo of the object with the sensor attached). In the case where the user takes a photo of the object, the MSM system can then use object recognition to pair a sensor to an object. For example, a user attaches a sensor to a coffee mug, the sensor is activated and starts flashing. The user can invoke a mobile device sensor pairing application developed for use with the MSM system and add the new object by taking a photo of the coffee mug. In the sensor pairing application the user can pick what object class most closely resembles the object (e.g. mug, glass, tea pot) based on an object recognition applied to the image. Once paired, the sensor detects properties relevant for that class of object (e.g. in one embodiment the sensor detects heat and tilt angle from a cup).

Sometimes it is necessary for the system to identify the user with which an object is interacting. In other situations identity won't matter or data can be processed entirely locally. When it is necessary for the system to identify the user with which an object is interacting, the system can automatically identify the user based on: a) physiological characteristics (e.g., a fingerprint or a hand tremor); and/or b) manual authentication (e.g. "my voice is my passphrase").

When a user, e.g., user B, is interacting with a sensor, e.g., sensor 102*b*, the sensor can transmit sensor data to a mobile data collection device 122 via transceiver 124 using wireless technology such as Wi-Fi, Bluetooth® or cellular. Alternatively, the sensor data can be transmitted to the transceiver 124 via other channels, e.g., wired or optical channel or via mechanical means such as a USB. The exemplary mobile data collection device 122 further includes a sensor data processor 126 that processes received sensor data and a mental state data service 128 that maintains mental state data and, in one embodiment, determines mental state data based on sensor data. The mobile data collection device can also communicate data to the attachable sensor 108 and the attachable sensor can produce an output based on the communicated data. The mobile data collection device can include memory (not shown) for storing sensor and mental state data. The mobile collection data device can be a device that is already in existence such as a smartphone or a security badge and tasked for this purpose or it can be a device whose primary purpose is operating with a MSM system.

The sensor can also transmit sensor data via the internet 110, or via other wired or wireless technology such as Bluetooth® or cellular. to a mental state data analysis engine 112. The mental state data analysis engine 112 includes a sensor data processor 114 that processes sensor data, a mental state data processor 116 that determines mental state data based on sensor data and an action/recommendation engine 118 that automatically acts based on mental state data.

Mental state data is processed sensor data that indicates specified mental states such as stress, boredom, anger, frustration, fatigue, happiness, and concentration. A mental state can be represented using a variety of text or graphical techniques including emoticons and use of color, sound, or temperature.

The most commonly used techniques for determining mental state include the use of textual information, facial expression, speech, body gestures, and physiological signals. Taking physiological signals as an example, such signals can include heart rate, skin conductance and temperature. In one embodiment an amplified and filtered physiological signal is fed as input into a sensor data processor for processing. In another embodiment, a headpiece also senses muscle and nerve activity via an electrode.

The processed data is transmitted, e.g., wirelessly, to the MSM system for storage, processing and feature extraction so as to allow determination of an associated mental state. The mental state system can use clustering and/or evaluation techniques to convert physiological sensor data to mental state data. In one embodiment, the MSM system can use a support vector machine to perform classification of physiological data and to derive mental state data. In an alternative embodiment, the MSM system can use linear discriminant analysis to classify observed physiological data into mental state categories. In still another embodiment, the MSM can use a k-means clustering algorithm to classify observed physiological data into mental state categories.

The mental state data analysis engine stores its data, e.g., sensor data with associated time, location, encrypted user ID and group ID along with mental state data, in database 120. The mental state data analysis engine 112 can communicate directly with the mobile data collection device 122, e.g., via a cellular channel as opposed to via the Internet. Similarly, in one embodiment the mental state data analysis engine 112 can communicate directly with a display 128, or it can communicate with the display via the Internet, to display mental state data. The display can be a display configured to display the mental state data to relevant members of a group or the whole group. For example, the display could be a large screen display in a common area. Alternatively the display could be a smaller display such as a mobile device, a display on a non-wearable object, or a display on a wearable device.

Figure 2:
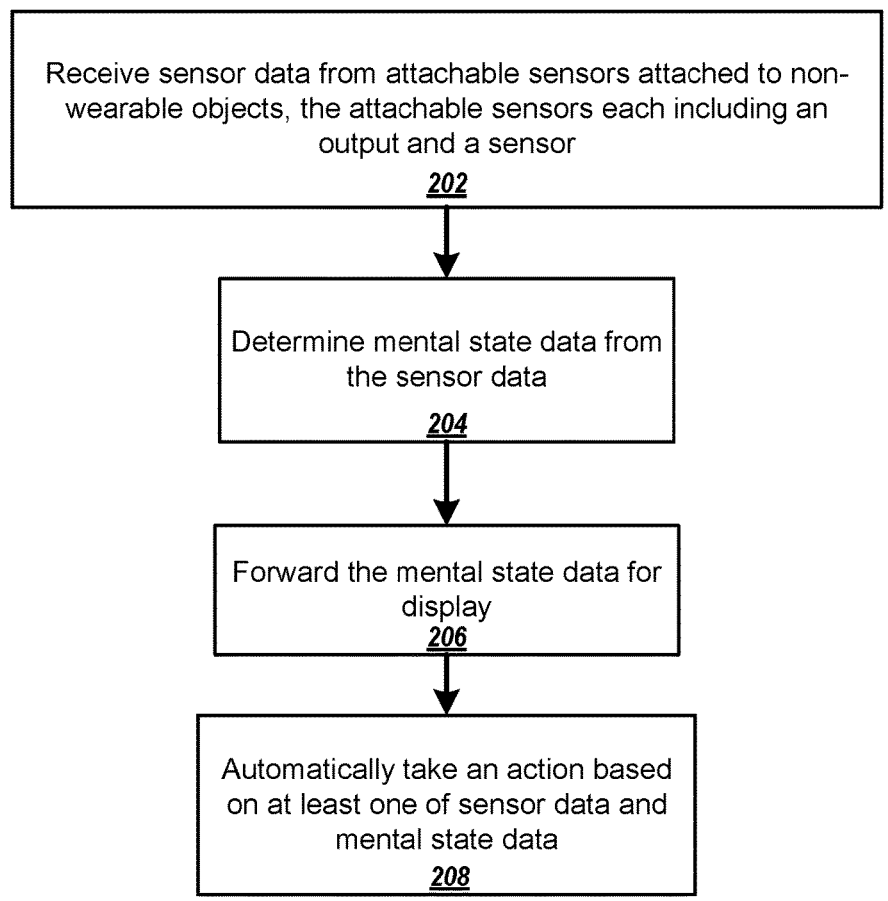
FIG. 2 is a flowchart of an exemplary method for determining mental state data based on sensor data.

FIG. 2 is a flowchart of an example method 200 for determining mental state data from sensor data garnered from attachable sensors. For convenience, the method 200 will be described as being performed by a system of one or more computers, located in one or more locations, and programmed appropriately in accordance with this specification. For example, a MSM system, e.g., the MSM system 100 of FIG. 1, appropriately programmed, can perform the method 200.

The method 200 includes receiving 202 sensor data from first and second attachable sensors attached to first and second non-wearable objects respectively. The first and second attachable sensors are configured to attach to a non-wearable object after the object has been manufactured. The first and second attachable sensors each include a sensor and an output configured to output sensor data or other data. The method 200 further includes: determining 204 mental state data from the sensor data; forwarding 206 the mental state data for display; and automatically taking an action 208 based on at least one of sensor data and mental state data.

Figure 3:
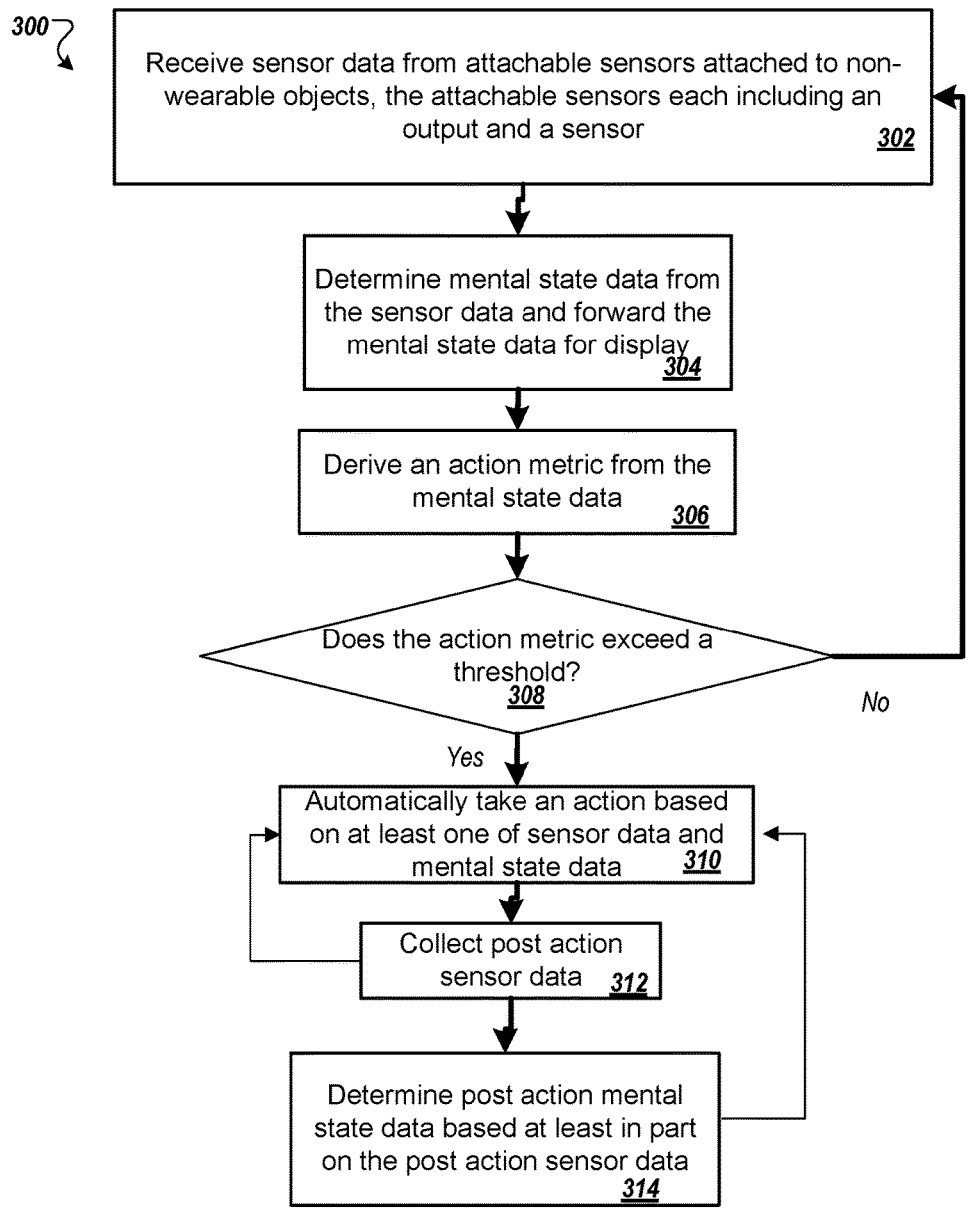
FIG. 3 is a flowchart of a method for determining mental state data based on sensor data according to an alternative embodiment.

FIG. 3 is a flowchart of an alternative embodiment of a method for determining mental state data from sensor data garnered from attachable sensors. The method 300 includes receiving 302 sensor data from first and second attachable sensors attached to first and second non-wearable objects respectively. In one embodiment, the first and second attachable sensors are configured to attach to a non-wearable object after the object has been manufactured. In another embodiment, the sensors may be embedded or otherwise attached to the object during manufacturing. The first and second attachable sensors each include a sensor and an output configured to output sensor data or other data. The method 300 further includes: determining 304 mental state data from the sensor data; forwarding 306 the mental state data for display; and deriving 306 an action metric from the mental state data. The method then determines 308 whether the action metric exceeds a threshold. If not, the method returns to receiving 302 sensor data.

If the action metric does exceed a threshold, the method automatically takes an action 310 based on at least one of the sensor data and the mental state data. The system can take a variety of actions such as: recommending an individual or group of individuals relocate or take a break, presenting soothing images, playing soothing music, recommending a break from the current task, or recommending exercise or talking to another member of the group. The method can further include: collecting 312 post action sensor data and determining 314 post action mental state data based at least in part on the post action sensor data. The method can then use at least one of the post action sensor data and the post action mental state data back when determining 310 what action to take automatically based at least one of sensor data and mental state data.

The sensors can include one or more of the following: microphones (detecting a variety of audio input including voice levels, tonality, shiver, mumbling, pauses, and rhythm); image and/or video cameras that can perform facial recognition and mental state classification (e.g., sad, surprised, focused), and that can detect for example body posture and/or pace; wearable sensors, touch sensors and software based sensors that detect for example key press, hardness, speed/pause, mistake interval, salt (sweat), heat, accuracy of use of a pointer or touchpad, amount of context switching (frequency and intention, breaks, type of application being worked on), posture and pace; environmental sensors (e.g., light sensors, air sensors, accelerometers and proximity detectors) for detecting proximity, noise, light, air quality, movement (jitteriness/stillness); sensors in pills that can detect for example biome status, chemical state, hormone levels, inflammation, blood count, and oxygen levels.

Sensors can be embedded directly into objects such as cups, water bottles, chairs, lamps, tables or in devices such as tablets, screens, and keyboards. Specially designed objects can have active sensing elements allowing users to communicate their emotional state. For example, a user can squeeze hard on a water bottle or shake a mouse cursor rapidly to communicate frustration. Sensors can also be embedded in adhesive sensor strips, which the user can attach to other objects and enable (non-sensing) objects to sense.

Figures 4A, 4B:
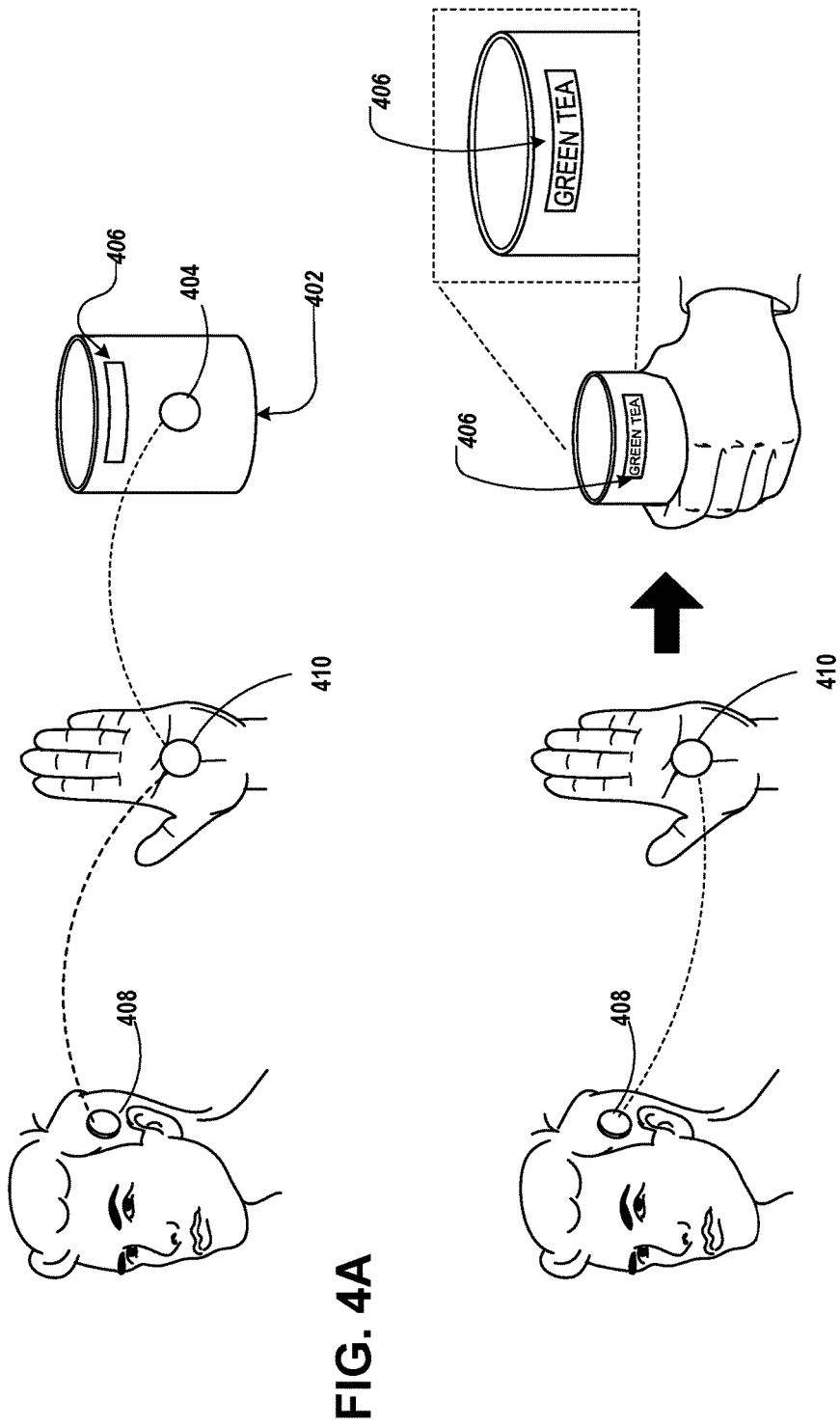
FIGS. 4A and 4B are schematics of a user interacting with a coffee mug having a sensor and a display.

FIGS. 4A and 4B are schematics of a user interacting with a coffee mug 402 having a receptor 404 and a display 406. The illustrated user also has a sensor 408, e.g., a biosensor embedded in a bone conduction headpiece adhesively attached near the user's ear, e.g., on the user's skin adjacent to or near a mastoid bone, and a wearable sticker 410, e.g., attached to the user's hand.

With reference to FIG. 4B, in operation the headpiece 408 can detect user data, e.g., physiological data, and transmit that data to a wearable sticker 410. When the user interacts with the object, the object's display 406 displays information that takes into account the user's sensor data and/or mental state data. For example, if the sensor data from sensor 408 indicates that the mental state of the user is stressed, the sensor 408 may communicate sensor data and/or mental state data to a wearable sticker/communication device 410 which in turn may communicate with an object, e.g., a mug. Then the mug may suggest that the user drink green tea instead of espresso. In addition or alternatively, the user can trigger the display to make a suggestion by asking a question (such as "what drink should I have?") that is detected by a sensor, e.g., a bone-conducting headpiece such as element 408. As shown, wearable sticker 410 is worn on the palm of a user's hand. In other examples, wearable sticker 410 may be worn elsewhere on a user (e.g., elsewhere on a limb, or on the body). In an alternative embodiment, sensor 408 may communicate directly with a receptor, e.g., receptor 404, on the object 406. In still another embodiment, receptor 404 is itself a sensor such that the wearable sticker 410 or even headpiece 408 may not be required.

Figure 5:
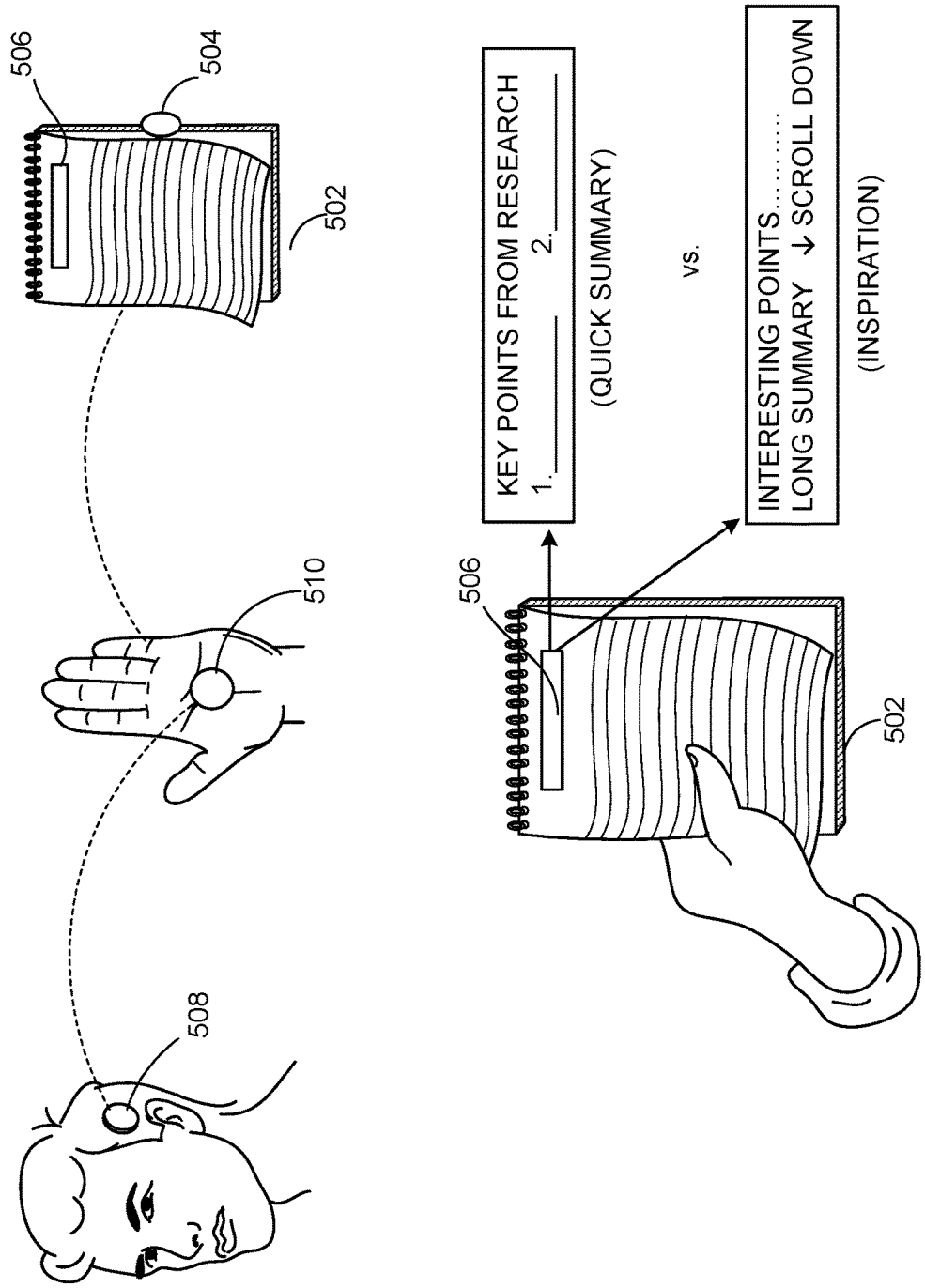
FIG. 5 is a schematic of a user interacting with a notebook having a sensor and a display.

FIG. 5 is a schematic of a user interacting with a notebook 502 (paper notebook or electronic notebook) having a receptor 504 and a display/screen implant 506. The illustrated user also has a sensor 508, e.g., a biosensor embedded in a bone conduction headpiece adhesively attached near the user's ear, and a wearable sticker/sensor 510, e.g., attached to the user's hand. In an alternative embodiment, sensor 508 may communicate directly with a receptor on the object 506. In operation, the headpiece 508 can detect user data, e.g., physiological data, and transmit that data to the wearable sticker 510. When the user interacts with the object, the display 506 displays information that takes into account the user's sensor data. For example, if the sensor data indicates that the mental state of the user is stressed, the notebook may summarize key points for the user to consider. Alternatively, if the sensor 508 detects data indicating that a user is bored, the display 506 may note interesting points/fun facts, e.g., from the discussion of from experts on the topic of discussion. Thus, one embodiment of the system adapts output on an object based on the emotional/mental state that it measures.

Software can also be used to obtain data relevant to a user's mental state. Software can be installed as a software keyboard (on phones and tablets) and as an application for a desktop operating system to determine a variety of signals such as typing speed, pause, or pointer focus. Software can also analyze existing video (API for video feeds) to determine the emotional state of many people at once. For example, a speaker at a conference or lecture can in real-time see if the students are confused or engaged, even if she can't see the faces of the students herself.

Figure 6B:
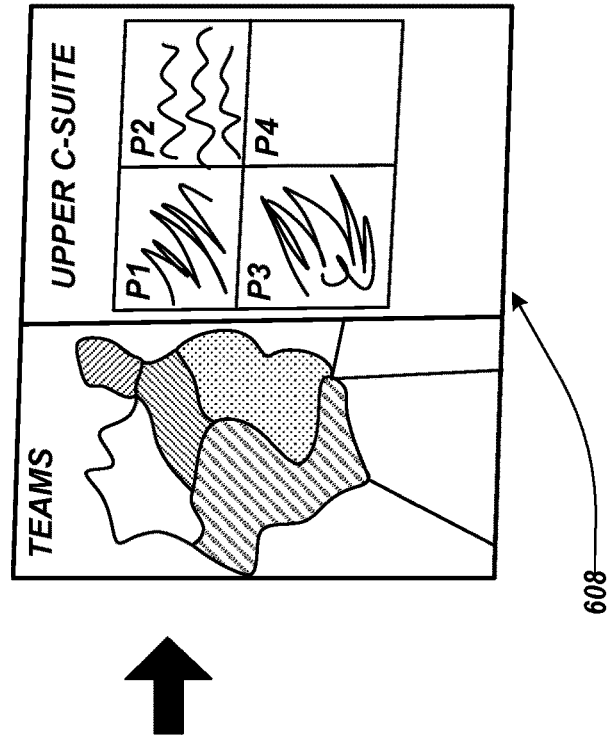
FIGS. 6A and 6B are schematics of exemplary elements of a system for collecting and displaying mental state data.
Figure 6A:
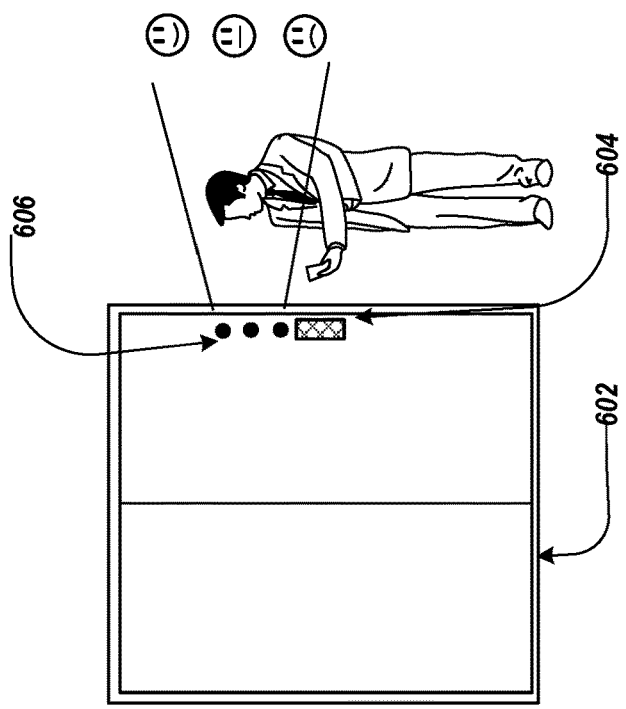

FIGS. 6A and 6B are schematics of exemplary elements of a system for collecting and displaying mental state data for groups. The system can gather the mental state data for a group of people (such as a work group, family, sports team, or hospital staff) and make that data available to a) all of the group members or b) only certain members (e.g. managers). For example, in FIG. 6A when a user badges in to (or out of) his place of employment, an entryway 602 may include a display 604 that presents the user with a question such as "how do you feel about work?" or "how are things going?" and the user can provide an answer upon entry via option 606. Such a simple survey system could be located in a variety of locations such as a kitchen, a break-room, meeting rooms or employee's desks.

The system can then make mental state data available with a time delay, e.g., with a delay of an hour, day or week (to avoid influencing the measured emotions as a result of users becoming self-conscious). The aggregate mental state data of groups can be displayed on a display 608 in a privacy preserving manner. The display 608, shown in FIG. 6B, can display the data as a heat-maps, a bubble-maps, or in other graphical or textual forms or via other forms of media. In one embodiment, the variance of emotional state and focus of different teams at a company can be displayed in relation to each other in a common area.

The mental state data of places can also be displayed. For example, one embodiment can embed sensors in tables and chairs and can display the places with highest and lowest stress. The places can be localized to a specific table or chair (e.g. a specific table at a restaurant) or larger areas such as a specific cafe or a specified city block.

The system can make aggregated mental state data available online in a privacy preserving manner. The system can also recommend places to go where other members of a group are relaxed. Embodiments provide a virtuous cycle, where the system measures frustration or fatigue of a user, recommends the user move to a place where members have a measured mental state with a better mental state metric, and again measure if the user's mental state metric improves after moving to the recommended place. This cycle tests the effectiveness of the system's recommendations (i.e. is a member's mental state better after the recommendations) and reinforces the effect (i.e. members learn where their mental state improves). The measured mental state data can also be displayed as a light and/or color on the member's badge, jewelry, watch, glasses, or in displays otherwise embedded in clothing.

Figure 7:
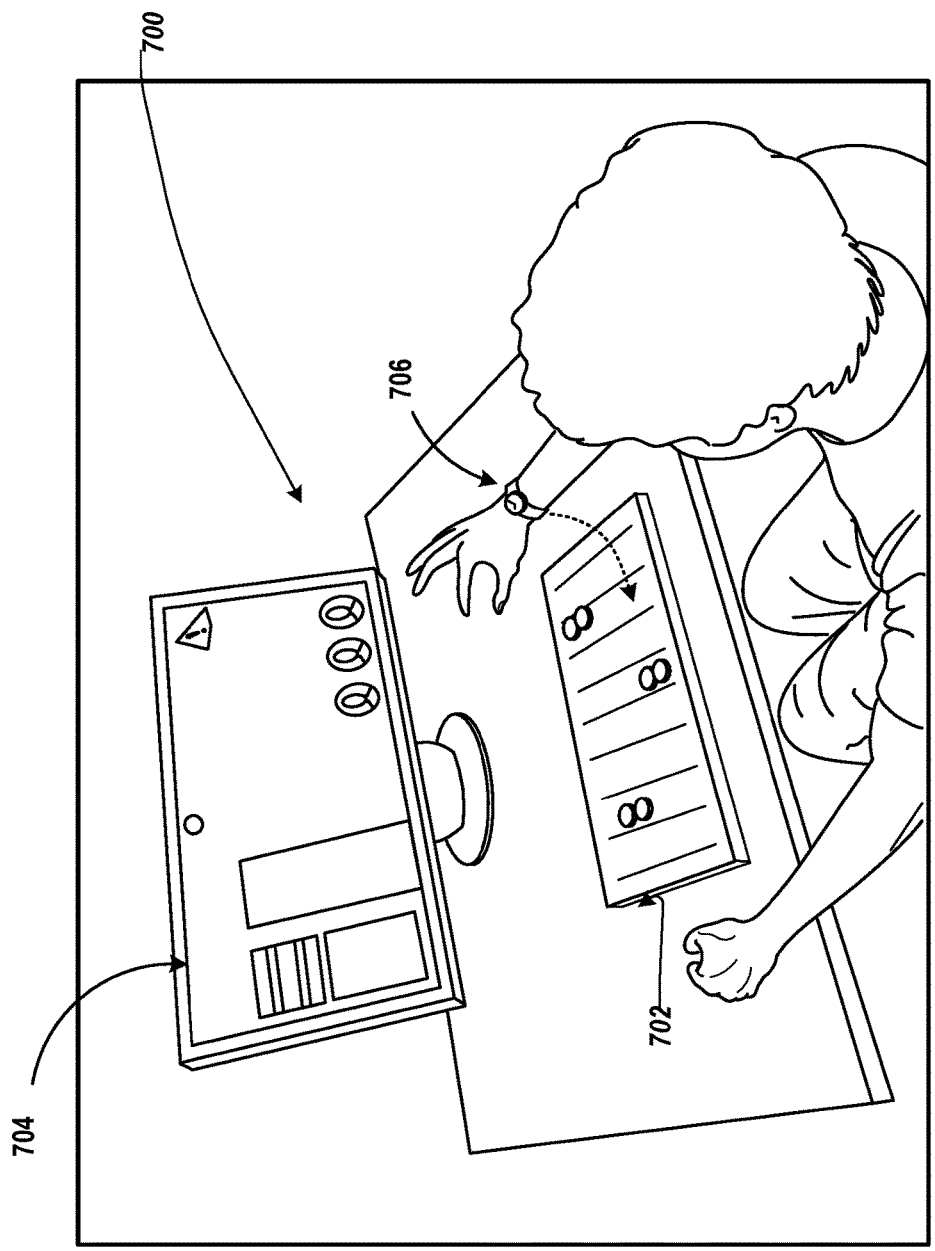
FIG. 7 is a schematic of a user interacting with an exemplary adaptive keyboard and display.
Figure 8:
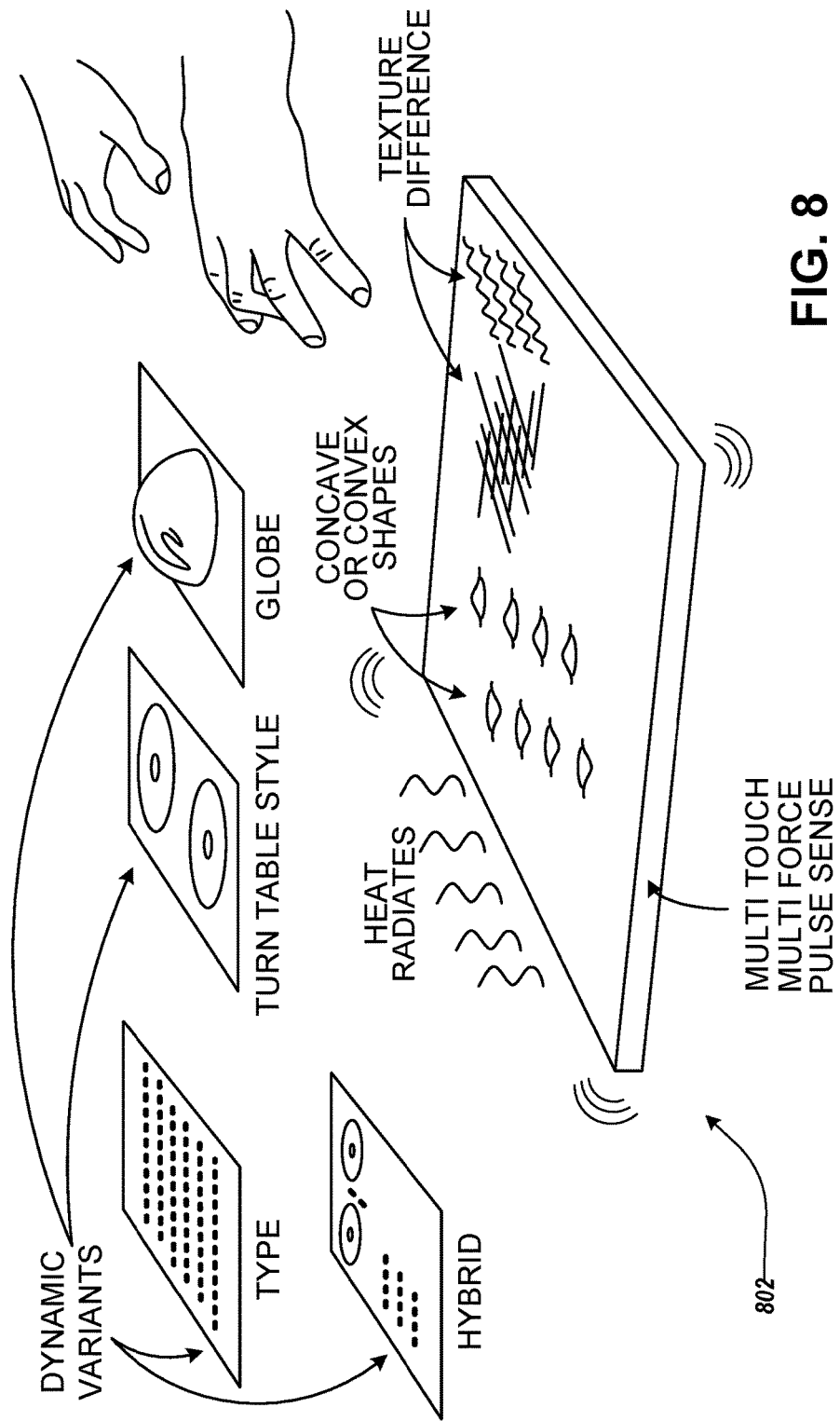
FIG. 8 is a schematic of an exemplary adaptive keyboard.
Figure 9:
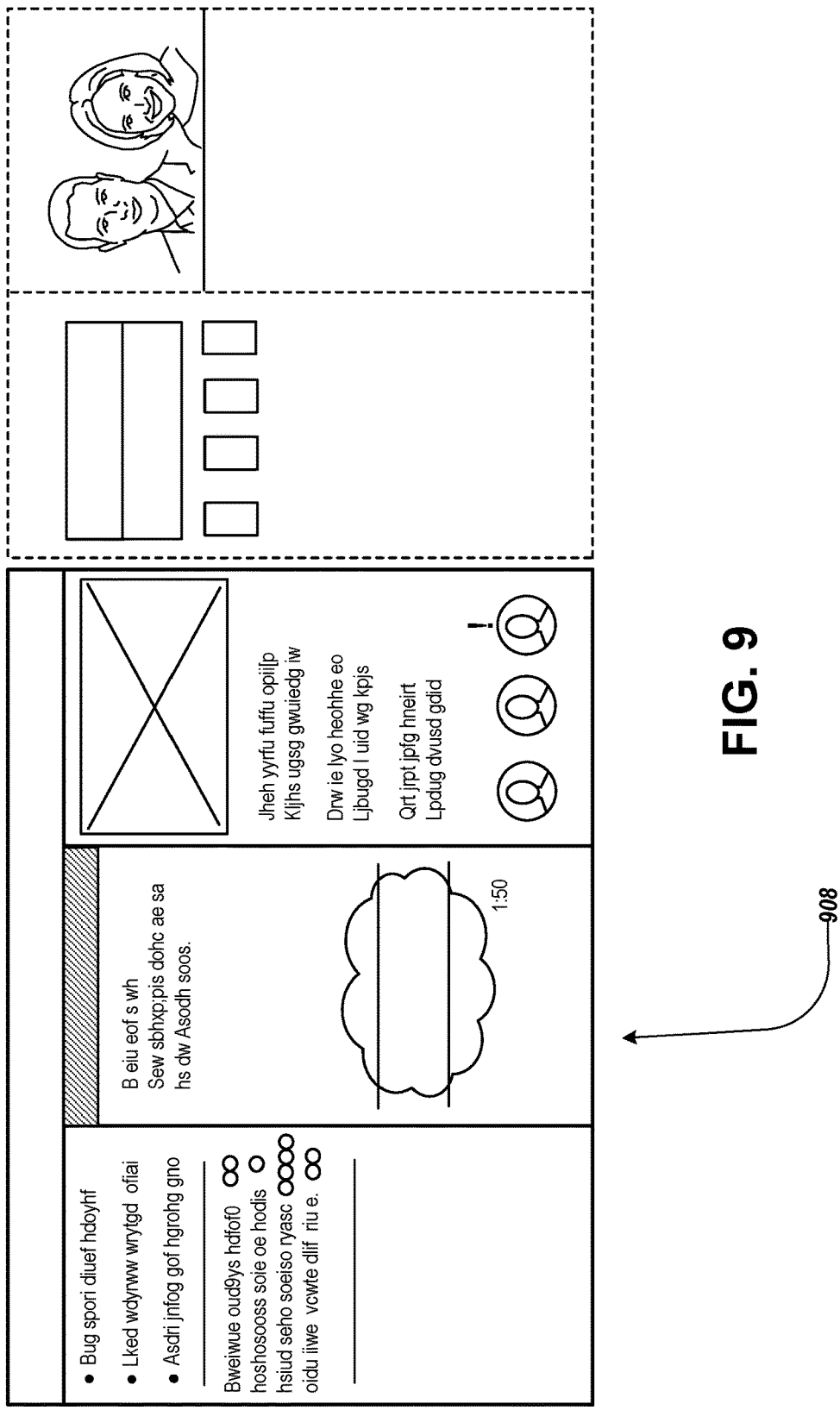
FIG. 9 is a schematic of an exemplary adaptive display. Like reference numbers and designations in the various drawings indicate like elements.

Embodiments can also provide user interface control based on user flow. For example, the system can gauge if the user is in a flow situation, i.e., if the user is highly focused on work, or in a more casual state with frequent breaks or context switching. The system can control what type of information gets presented in the user interface. FIG. 7 is a schematic of a user interacting with an exemplary system 700 including adaptive keyboard 702 and display 704. As illustrated, the user has a smart-watch 706 with sensors. FIG. 8 is a schematic of an exemplary adaptive keyboard 802, and FIG. 9 is a schematic of an exemplary adaptive display 908. As illustrated in FIG. 7, a user's smart-watch 704 sends sensor data to an adaptive keyboard and display system 700 which adapts in light of sensor data. For example, with reference to FIG. 8 the keyboard 802 can change presentations, e.g. from typing to turn table to a globe to a hybrid based on the user's mental state data. Indeed, the adaptive keyboard can change temperature, shape or texture or it can vibrate through the use of haptics.

With reference to FIG. 9, the system can delay notifications and hide non-important applications or parts of the display 908 while the user is in a focused mental state. The figure shows a monitor with a set of window components. The MSM system introduces new windows on the right based on user state and context. The following are a set of examples. The MSM system may detect that a user is stressed. As a result, the system may introduce pictures into view (e.g. pictures of family/friends or a calming landscape or the system prompts a break. In another example, the system may detect that a user is in a "flow state". i.e., in a focused state while coding or writing. As a result, the system blocks or delays incoming notifications (e.g. from email platforms or browsers), for example, until there is a determination made that the user has exited the flow state or has an important meeting to attend. In yet another example, the system detects that a user is multi-tasking but slowly losing focus. As a result, the system can hide/show elements to better focus the user (e.g. the system can hide browser tabs or lower the volume on music). As still another example, the system may detect that a user has been assigned 6 tasks (e.g. review patents, go to meeting . . . ) and the system can change the display in a time-synchronized manner where the relevant documents are opened and presented at the relevant time then hidden once the task is complete or when time is up.

The system can also control visual qualities for the user whose emotional level is being measured. For example, the system can turn the user's screen slightly red when the user is stressed, or mark the top bar (menu bar) on their screen in a blue stripe to signal to coworkers that the user is in a focused state. Similarly, certain elements of the screen can fade out, if the user is not paying attention to the primary object, to facilitate focus. The system can control user input timing. For example, the system can delay typing and touch inputs to encourage the user to slow down.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network. The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers. Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Also the MSM system can use a cascade of data gathering, meaning if ideal data is not available, the system may use the next best form of data. Sensors are becoming more common in clothing and other textiles, e.g., furniture covering. Indeed it has become possible to weave touch and gesture interactivity into any textile using standard, industrial looms. Everyday objects such as clothes and furniture can be transformed into interactive surfaces. If no wearable is present, the MSM system can use off-person sensors.

What is claimed is:

1. A system comprising:
one or more computers and one or more storage devices on which are stored instructions that are operable, when executed by the one or more computers, to cause the one or more computers to perform operations for determining mental state data, the operations comprising
(a) receiving, at a mental state measurement system having a mental state data processor, sensor data from a first attachable sensor attached to a first non-wearable object and a second attachable sensor attached to a second non-wearable object, the first and second attachable sensors each including an output and a sensor;
(b) determining, by the mental state data processor, mental state data from the sensor data;
(c) forwarding, by the mental state measurement system, mental state data for display of a representation of a mental state;
(d) deriving, by an action recommendation engine, an action metric from the mental state data;
(e) comparing, by an action recommendation engine, the action metric to a threshold;
(f) automatically taking an action when the action metric exceeds the threshold, the action comprising at least one of
auto-locking a display,
delaying a notification, and
hiding parts of a display;
(g) collecting, via a sensor data processor, post action sensor data;
(h) determining, by a mental state data processor, post action mental state data based at least in part on the post action sensor data; and
(i) forwarding the post action mental state data, to a display, for display of a representation of a mental state.

2. The system of claim 1, the operations further comprising using at least one of the post action sensor data and the post action mental state data in determining which action to take automatically in the future.

3. The system of claim 1, wherein the first attachable sensor is configured to detect sensor data associated with at least a first member of a group and the second attachable sensor is configured to detect sensor data associated with at least a second member of the group.

4. The system of claim 1, the operations further comprising:
(a) automatically taking an action based on the mental state information.

5. The system of claim 4, wherein automatically taking an action comprises providing a recommendation, by the mental state measurement system, to at least one member of the group to relocate based on the mental state data.

6. The system of claim 1, wherein the first attachable sensor provides an output to the user in response to at least one of mental state data and sensor data.

7. The system of claim 1, the operations further comprising altering properties of a communication device associated with a member of the group in response to at least one of mental state data and sensor data associated with the member.

8. The system of claim 1, wherein the group is a group of people associated with a location and the operations further comprise displaying the mental state data for a location based on the mental state of the group associated with that location.

9. The system of claim 1, the operations further comprising receiving sensor data from a sensor that is connected to a bone conduction device.

10. The system of claim 1, wherein the non-wearable objects are objects that do not have sensors prior to attaching the attachable sensors.

11. The system of claim 1, where the first attachable sensor is attached using an adhesive strip.

12. A computer-implemented method of determining mental state data, the method comprising:
 (a) receiving, at a mental state measurement system having a mental state data processor, sensor data from a first attachable sensor attached to a first non-wearable object and a second attachable sensor attached to a second non-wearable object, the first and second attachable sensors each including an output and a sensor;
 (b) determining, by the mental state data processor, mental state data from the sensor data;
 (c) forwarding, by the mental state measurement system, mental state data for display of a representation of a mental state;
 (d) deriving, by an action recommendation engine, an action metric from the mental state data;
 (e) comparing, by an action recommendation engine, the action metric to a threshold
 (f) automatically taking an action when the action metric exceeds the threshold, the action comprising at least one of
  auto-locking a display,
  delaying a notification, and
  hiding parts of a display;
 (g) collecting, via a sensor data processor, post action sensor data;
 (h) determining, by a mental state data processor, post action mental state data based at least in part on the post action sensor data;
 (i) forwarding the post action mental state data for display of a representation of a mental state;
 (j) using at least one of the post action sensor data and the post action mental state data in determining an action to take automatically in the future; and
 (k) providing an output to the first attachable sensor in response to at least one of mental state data and sensor data.

13. The method of claim 12, wherein the first attachable sensor is further configured to detect sensor data associated with at least a first member of a group and the second attachable sensor further is configured to detect sensor data associated with at least a second member of the group.

14. One or more computer-readable storage media encoded with instructions that, when executed by one or more computers, cause the one or more computers to perform operations comprising
 (a) receiving, at a mental state measurement system having a mental state data processor, sensor data from a first attachable sensor attached to a first non-wearable object and a second attachable sensor attached to a second non-wearable object, the first and second attachable sensors each including an output and a sensor;
 (b) determining, by the mental state data processor, mental state data from the sensor data;
 (c) forwarding, by the mental state measurement system, mental state data for display of a representation of a mental state,
 (d) deriving, by an action recommendation engine, an action metric from the mental state data;
 (e) comparing, by an action recommendation engine, the action metric to a threshold
 (f) automatically taking an action when the action metric exceeds the threshold, the action comprising at least one of
  auto-locking a display,
  delaying a notification, and
  hiding parts of a display;
 (g) collecting, via a sensor data processor, post action sensor data;
 (h) determining, by a mental state data processor, post action mental state data based at least in part on the post action sensor data; and
 (i) forwarding the post action mental state data for display of a representation of a mental state.

15. The computer-readable non-transitory storage media of claim 14 wherein the first attachable sensor provides an output to the user in response to at least one of mental state data and sensor data.

16. The computer-readable non-transitory storage media of claim 14, wherein the first attachable sensor further configured to detect sensor data associated with at least a first member of a group and the second attachable sensor further configured to detect sensor data associated with at least a second member of the group.

17. A system comprising:
 a mobile data collection device configured to obtain and transmit sensor data from an attachable sensor attached to a non-wearable object, the attachable sensor including an output and a sensor,
 the mobile data collection devices comprising:
  a sensor data processor that processes received sensor data;
  a mental state data service that maintains mental state data; and
  a mental state data analysis engine configured to receive sensor data from the mobile data collection device, analyze the sensor data and take an action, the mental state data analysis engine comprising:
   a sensor data processor that process the sensor data;
   a mental state data processor that determines mental state data based on the sensor data; and an action engine that automatically takes an action based on the mental state data, wherein the action comprises at least one of
auto-locking a display,
delaying a notification, and
hiding parts of a display.

\* \* \* \* \*